United States Patent [19]

Ingram et al.

[11] Patent Number: 5,028,539

[45] Date of Patent: Jul. 2, 1991

[54] ETHANOL PRODUCTION USING ENGINEERED MUTANT E. COLI

[75] Inventors: Lonnie O. Ingram, Gainesville, Fla.; David P. Clark, Carbondale, Ill.

[73] Assignee: The University of Florida, Gainesville, Fla.

[21] Appl. No.: 274,075

[22] Filed: Nov. 21, 1988

Related U.S. Application Data

[63] Continuation-in-part of Ser. No. 239,099, Aug. 31, 1988, abandoned.

[51] Int. Cl.$^5$ .......................... C12P 7/06; C12N 1/20; C12N 9/02
[52] U.S. Cl. ................................... 435/161; 435/189; 435/190; 435/252.33; 435/172.1; 435/172.3; 935/60; 935/73
[58] Field of Search ...................... 435/161, 170, 172.3, 435/320; 536/27; 935/27, 42, 73

[56] References Cited

PUBLICATIONS

Fried, V. A., A. Novick (1973) "Organic Solvents as Probes for the Structure and Function of the Bacterial Membrane: Effects of Ethanol on the Wild Type and an Ethanol-Resistant Mutant of *Escherichia coli* K-12," J. Bacteriol. 114(1):239-248.

Ingram, L. O. (1976) "Adaptation of Membrane Lipids to Alcohols," J. Bacteriol. 125(2):670-678.

Ingram, L. O., N. S. Vreeland (1980) "Differential Effects of Ethanol and Hexanol on the *Escherichia coli* Cell Envelope," J. Bacteriol. 144(2):481-488.

Ingram, L. O., T. M. Buttke (1984) "Effects of Alcohols on Micro-Organisms," In *Advances in Microbial Pathology*, vol. 25, Academic Press, London; pp. 254-295.

Ingram, L. O. T. Conway, D. P. Clark, G. W. Sewell, and J. F. Preston (1987) "Genetic Engineering of Ethanol Production in *Escherichia coli*," Appl. Env. Microbiol. 53(10):2420-2425.

Conway, T., Y. Osman, J. I. Konna, E. M. Hoffmann, and L. O. Ingram (1987) "Promoter and Nucleotide Sequences of the *Zymomonas mobilis* Pyruvate Decarboxylase," J. Bacteriol. 169(3):949-954.

Brau, B. and H. Sahm (1986) "Cloning and Expression of the Structural Gene for Pyruvate Decarboxylase of *Zymomonas mobilis* in *Escherichia coli*," Arch. Microbiol. 144:296-301.

Clark et al., J. Mol. Evol., vol. 25(2); pp. 151-8 (1987).

Conway et al., J. Bacteriology, vol. 169(3); pp. 949-954 (1987).

*Primary Examiner*—Robin L. Teskin
*Attorney, Agent, or Firm*—Saliwanchik & Saliwanchik

[57] ABSTRACT

The subject invention concerns novel means and materials for producing ethanol as a fermentation product. Mutant *E. coli* are transformed with a gene coding for pyruvate decarboxylase activity. The resulting system is capable of producing relatively large amounts of ethanol from a variety of biomass sources.

4 Claims, No Drawings

ETHANOL PRODUCTION USING ENGINEERED MUTANT E. COLI

This is a continuation in part of copending application Ser. No. 239,099, filed Aug. 31, 1988, now abandoned.

BACKGROUND OF THE INVENTION

During glycolysis, cells convert simple sugars, such as glucose, into pyruvic acid, with a net production of ATP and NADH. In the absence of a functioning electron transport system for oxidative phosphorylation, at least 95% of the pyruvic acid is consumed in short pathways which regenerate NAD+, an obligate requirement for continued glycolysis and ATP production. The waste products of these NAD+ regeneration systems are commonly referred to as fermentation products (Ingram, L. O., T. Conway, D. P. Clark, G. W. Sewell, and J. F. Preston [1987] "Genetic Engineering of Ethanol Production in *Escherichia coli,*" App. and Env. Microbiol. 53:2420-2425).

Microorganisms are particularly diverse in the array of fermentations products which are produced by different genera (Krieg, N. R., and J. G. Holt, eds. [1984] *Bergey's manual of systematic bacteriology.* The Williams & Wilkins Co., Baltimore). These products include organic acids, such as lactate, acetate, succinate, and butyrate, as well as neutral products, such as ethanol, butanol, acetone, and butanediol. Indeed, the diversity of fermentation products from bacteria has led to their use as a primary determinant in taxonomy (Krieg and Holt [1984], supra).

End products of fermentation share several fundamental features. They are relatively nontoxic under the conditions in which they are initially produced but become more toxic upon accumulation. They are more reduced than pyruvate because their immediate precursors have served as terminal electron acceptors during glycolysis. The microbial production of these fermentation products forms the basis for our oldest and most economically successful applications of biotechnology and includes dairy products, meats, beverages, and fuels. In recent years, many advances have been made in the field of biotechnology as a result of new technologies which enable researchers to selectively alter the genetic makeup of some microorganisms.

*Escherichia coli* is an important vehicle for the cloning and modification of genes for biotechnology and is one of the most important hosts for the production of recombinant products. In recent years, the range of hosts used for recombinant DNA research has been extended to include a variety of bacteria, yeasts, fungi, and some eukaryotic cells. The invention described here relates to the use of recombinant DNA technology to elicit the production of specific useful products by a modified host.

The DNA used to modify the host of the subject invention is isolated from *Zymononas mobilis. Z. mobilis* is a microorganism with unusual metabolic characteristics which is commonly found in plant saps and in honey. *Z. mobilis* has long served as a natural inocula for the fermentation of the Agave sap to produce pulque (an alcohol-containing Mexican beverage) and as inocula for palm wines. This organism is also used for fuel ethanol production and has been reported capable of ethanol production rates which are substantially higher than that of yeasts.

Although *Z. mobilis* is nutritionally simple and capable of synthesizing amino acids, nucleotides and vitamins, the range of sugars metabolized by this organism is very limited and normally consists of glucose, fructose and sucrose. Substrate level phosphorylation from the fermentation of these sugars is the sole source of energy for biosynthesis and homeostasis. *Z. mobilis* is incapable of growth even in rich medium such as nutrient broth without a fermentable sugar.

*Z. mobilis* is an obligately fermentative bacterium which lacks a functional system for oxidative phosphorylation. This organism, like *Saccharomyces cerevisiae*, produces ethanol and carbon dioxide as principal fermentation products. *Z. mobilis* produces ethanol by a short pathway which requires only two enzymatic activities: pyruvate decarboxylase and alcohol dehydrogenase. Pyruvate decarboxylase is the key enzyme in this pathway which diverts the flow of pyruvate to ethanol. Pyruvate decarboxylase catalyzes the nonoxidative decarboxylation of pyruvate to produce acetaldehyde and carbon dioxide. Two alcohol dehydrogenase isozymes are present in this organism and catalyze the reduction of acetaldehyde to ethanol during fermentation, accompanied by the oxidation of NADH to NAD+. Although bacterial alcohol dehydrogenases are common in many organisms, few bacteria have pyruvate decarboxylase. Attempts to modify *Z. mobilis* to enhance its commercial utility as an ethanol producer have met with very limited success.

The gene coding for pyruvate decarboxylase in *Z. mobilis* has been cloned, characterized, and expressed in *E. coli* (Brau, B., and H. Sahm [1986] "Pyruvate decarboxylase from *Zymomonas mobilis.* Isolation and partial characterization," Arch. Microbiol. 146:105-110; Conway, T., Y. A. Osman, J. I. Konnan, E. M. Hoffmann, and L. O. Ingram [1987] "Promoter and nucleotide sequences of the *Zymomonas mobilis* pyruvate decarboxylase," J. Bacteriol. 169:949-954). The subject invention relates to the creation and expression of a novel system coding for the production of ethanol.

BRIEF SUMMARY OF THE INVENTION

The invention described here concerns the construction of a unique metabolic system for ethanol production which includes the introduction of the pyruvate decarboxylase activity into cells with constitutive and hyperproducing dehydrogenase gene mutations. The novel pathway utilizes the enhanced alcohol dehydrogenase activity of a mutant *E. coli* combined with the pyruvate decarboxylase activity resulting from the introduction of the pyruvate decarboxylase gene into the mutant *E. coli.* This system is capable of effectively diverting pyruvate to ethanol during growth under both aerobic and anaerobic conditions.

Also described here are novel strains of *E. coli* which contain the ethanol-producing pathway.

DETAILED DESCRIPTION OF THE INVENTION

Certain bacteria and other simple organisms are capable of actively metabolizing a wide variety of substrates, including hexoses, pentoses, and lactose. The invention described here allows the use of a recombinant strain of *E. coli* for the production of ethanol from under-utilized sources of biomass, such as hemicellulose (xylose, arabinose, etc.), which represents a major portion of wood and inedible plant parts, and whey (lactose), as well as from other biomass sources.

Described here is a novel system by which cells produce ethanol. The system comprises the *Z. mobilis* gene coding for pyruvate decarboxylase activity, together with appropriate regulatory sequences, introduced into cells with constitutive and hyperproducing alcohol dehydrogenase gene mutations. The regulatory sequences may consist of promoters, inducers, operators, ribosomal binding sites, terminators, and/or other regulatory sequences. Using the materials and methods described herein, significant amounts of ethanol can be produced in recombinants under both aerobic and anaerobic conditions.

The conversion of a host organism to ethanolic fermentation can be used to enhance the production of a variety of recombinant products using the host's expression system. The maintenance of function in these products is related to the pH of the broth during growth in dense culture. The extent of this acidification per unit of cell protein is minimized by the production of ethanol rather than of organic acids. Oxygen transfer is frequently a major limitation during the growth of dense cultures of microorganisms, and it is this limitation which results in acid production and pH drift of the growth medium. In recombinants expressing the novel pathway, part of the pyruvate is diverted from glycolysis to acetaldehyde and reoxidizes NADH to produce ethanol, a less damaging product of metabolism. Strains containing both functional respiratory chains for oxidative phosphorylation and ethanol production enzymes can be grown to even higher cell densities because of the operation of both systems during the regeneration of $NAD^+$ and a reduction in acidic waste products. Such inherent flexibility results in less stringent process-control requirements, as well as increased yields of recombinant products.

This work demonstrates that recombinants can be developed for commercial ethanol production, and it illustrates the feasibility of drastic changes in metabolic flow for the future development of novel products from microorganisms. In addition, strains containing the novel pathway grow to higher cell densities than do the parent organisms under anaerobic conditions with glucose and offer the potential for the increased production of recombinant products in microorganisms while reducing complications associated with acid production.

MATERIALS AND METHODS

Organisms and growth conditions. *E. coli* TC4 (Conway, T., Y. A. Osman, J. I. Konnan, E. M. Hoffman, and L. O. Ingram [1987] "Promoter and nucleotide sequences of the *Zymomonas mobilis* pyruvate decarboxylase," J. Bacteriol. 169:949-954) and plasmid-containing derivatives were used in the present study. Plasmids containing the pyruvate decarboxylase gene (pLOI276) have been described previously (Conway and Osman et al. [1987], "Promoter and nucleotide sequences...," supra).

In order to practice the invention, it is also necessary to have microorganisms with the capacity for producing high levels of alchol dehydrogenase. For example, the *E. coli* strains DC862adhC and DC863adhC adHR have hyperproducing alcohol dehydrogenase gene mutations. These microorganisms have been deposited with the American Type Culture Collection (ATCC), 12301 Parklawn Drive, Rockville, Md. 20852 USA. The deposits were made on Dec. 29, 1988. The cultures were assigned the following accession numbers by the repository:

| Culture | Accession number | Deposit date |
|---|---|---|
| *E. coli* DC862adhC | ATCC 53846 | December 29, 1988 |
| *E. coli* DC863adhC adHR | ATCC 53847 | December 29, 1988 |

The subject cultures have been deposited under conditions that assure that access to the cultures will be available during the pendency of this patent application to one determined by the Commissioner of Patents and Trademarks to be entitled thereto under 37 CFR 1.14 and 35 USC 122. The deposits are available as required by foreign patent laws in countries wherein counterparts of the subject application, or its progeny, are filed. However, it should be understood that the availability of the deposits does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

The existence of microorganisms which produce high levels of alcohol dehydrogenase has been recognized and described in Clark, D. P. and M. L. Rod (1987) J. Mol. Evol. 25:151-158.

Strains and growth conditions. Plasmids pUC18 and pUC19 (Yanisch-Perron, C., J. Vieira, and J. Messing [1985] "Improved M13 phage cloning vectors and host strains: nucleotide sequence of the M13mp18 and pUC19 vectors," Gene 33:103-119), pLOI204 (Conway, T., M. O. -K. Byung, and L. O. Ingram [1987] "Expression vector for *Zymomonas mobilis*," Appl. Environ. Microbiol. 53:235-241), and pLOI295 (Ingram et al. [1987], supra) have been previously described.

Cultures were grown at 37° C. in Luria broth (Luria, S. E. and M. Delbruck [1943] "Mutations of bacteria from virus sensitivity to virus resistance," Genetics 28:491-511) containing 50 g of glucose per liter. Cells for enzyme analyses and inocula for fermentation studies were grown in tubes (13 by 100 mm) containing 3 ml of broth at 37° C. in a tube rotator. Overnight cultures were diluted 100-fold into fresh medium. Aerobic cultures (50 ml of broth in 250 ml flasks) were shaken in a reciprocating water bath (120 oscillations per min). Anaerobic cultures were grown in stoppered serum bottles (100 ml of broth in 130 ml bottles) with gyratary agitation (150 rpm) in a 37° C. incubator. Anaerobic cultures were vented with a 25-gauge needle to allow escape of gaseous fermentation products.

Growth was monitored spectrophotometrically with a Spectronic 70 spectrophotometer (Bausch & Lomb, Inc., Rochester, N.Y.) at 550 nm. Disposable culture tubes (10 by 75 mm) were used as cuvettes. One absorbance unit under our conditions contained approximately 0.25 mg of cellular protein per ml. Growth was measured at $A_{550}$; 1.0 absorbance unit is equivalent to 0.25 mg of total cell protein per ml.

Genetic techniques. Recombinants were selected on solid media (1.5% agar) containing 2 g of glucose per liter and appropriate antibiotics. Recombinants containing functional ethanologenic genes from Z. mobilis were identified by their growth as oversized colonies on Luria agar plates containing glucose and were confirmed by their poor growth on Luria agar plates lacking glucose and by the expression of alcohol dehydrogenase on aldehyde indicator medium.

Enzyme assays. Cells were disrupted, heat-inactivated, and assayed for pyruvate decarboxylase activity (thermostable) as described previously (Conway and Osman et al. [1987] "Promoter and nucleotide sequences. . . ," supra). Cells were prepared and assayed for alcohol dehydrogenase II activity in the direction of ethanol oxidation as described previously, except that cells were washed and disrupted in 30 mM potassium phosphate buffer to which solid ferrous ammonium sulfate (final concentration, 0.5 mM) and sodium ascorbate (10 mM) had been freshly added as described by Neale et al. (Neale, A. D., R. K. Scopes, J. M. Kelly, and R. E. H. Wettenhall [1986] "The two alcohol dehydrogenases of *Zymomonas mobilis*: purification by differential dye ligand chromatography, molecular characterization and physiological role," Eur. J. Biochem. 154:119-124).

Analysis of fermentation products. Fermentation products were determined in clarified broth with a Millipore/Waters high-performance liquid chromatograph (Millipore Corp., Bedford, Mass.) equipped with a refractive index monitor and an electronic integrator. Separations were performed on an Aminex HPX-87H column (300 by 7.8 mm) purchased from Bio-Rad Laboratories, Richmond CA, at 65° C. at a flow rate of 0.25 ml/min (100 µl injection volume). Peaks were identified by using authentic standards. The two peaks eluting before glucose and the later unknown peak eluting at 45.4 to 45.8 min are components of uninoculated medium.

Following are examples which illustrate procedures, including the best mode, for practicing the invention. These examples should not be construed as limiting. All percentages are by weight and all solvent mixture proportions are by volume unless otherwise noted.

EXAMPLE 1

Strain construction

The sizes of the structural gene coding for pyruvate decarboxylase is 1.7 kilobases, and this gene encodes a protein with a molecular weight of 60,000. This gene is located on derivatives of pUC18 under the control of the lac promoter. A plasmid containing the pyruvate decarboxylase gene was created as described in Conway et al. (Conway, T., Y. A. Osman, J. I. Konnan, E. M, Hoffmann, and L. O. Ingram [1987] "Promoter and nucleotide sequences of the *Zymomonas mobilis* pyruvate decarboxylase," J. Bacteriol. 169:949-954). Clones were selected for resistance to ampicillin and for the presence and expression of alcohol dehydrogenase activity on a newly developed pararosaniline-ethanol indicator plate which detects the production of aldehydes. Clones containing the indicated construction grew poorly on the surface of Luria agar plates (aerobic) in the absence of added glucose but grew to much higher densities than the plasmid-free strain on agar plates containing 2% glucose. Recombinants containing the pyruvate decarboxylase gene were readily detected as larger, more opaque colonies on Luria agar plates (aerobic) containing glucose.

EXAMPLE 2

Expression of Z. mobilis genes in E. coli

Pyruvate decarboxylase was expressed at high levels in *E. coli* under the control of the lac promoter singly. During growth of *E. coli* in the presence of glucose, the specific activities of the Z. mobilis enzymes declined by approximately 50%, which is consistent with glucose repression of the lac promoter.

EXAMPLE 3

Fermentation of glucose by recombinant strains

Expression of the pyruvate decarboxylase gene in mutant *E. coli* resulted in the production of ethanol as the primary fermentation product during anaerobic growth. The parent strain produced succinate (1.5 mM), lactate (18 mM), and acetate (7 mM) as major fermentation products. With pLOI276 carrying the gene coding for pyruvate decarboxylase, an ethanol peak is clearly evident. This higher level of ethanol results from the combined activities of the pyruvate decarboxylase from Z. mobilis and the mutant *E. coli* alcohol dehydrogenase. Thus, the fermentation of this organism was converted to the equivalent of those of *S. cerevisiae* and Z. mobilis.

High cell densities are also achieved during mixed growth conditions with moderate agitation or stirring of culture vessels in which gas exchange is not restricted. Under these conditions, a final pH of 6.3 or above was observed, depending upon the extent of aeration.

EXAMPLE 4

Growth of recombinant strains containing the pyruvate decarboxylase enzyme from Z. mobilis Shifting the catabolism of glucose to the production of ethanol also affected growth yield and pH drift of the growth medium. Although fermentation products are relatively nontoxic, they may accumulate to toxic levels during fermentation. During anaerobic growth in bottles containing Luria broth containing 10% glucose, the plasmid-free strain achieved a final density of 0.25 mg of cell protein per ml after 48 hr, with a final pH of 4.4. The cell density increased by twofold in the strain carrying pLOI276 (carrying the gene coding for pyruvate decarboxylase), with a final pH of 4.5.

EXAMPLE 5

Effects of ethanologenic enzymes on the acidification of broth during growth

The pH fell rapidly during the first 6 hr of growth of strain TC4 lacking a plasmid but declined more slowly in derivatives containing the ethanologenic enzymes. Although the recombinants reached a higher final cell density, the pH of the broth from the recombinants grown under both anaerobic and aerobic conditions for 24 hr was less acidic than that of the broth from strain TC4 lacking ethanologenic enzymes.

The reduced rate and extent of acidification in recombinants accompanied by increased cell growth suggested that the fall in pH was a major factor limiting growth even under highly aerobic conditions. This hypothesis was supported by an 85% increase in the final cell density of strain TC4 (lacking a plasmid) grown in medium supplemented with a 1/10 volume of 1M sodium phosphate buffer (pH 7.0). Lower levels of buffer addition resulted in intermediate levels of growth.

EXAMPLE 6

Effects of ethanologenic enzymes on fermentation products

Under aerobic conditions, acetate was the primary fermentation product that accumulated during the growth of strain TC4 lacking a plasmid in rich medium, with no detectable ethanol. The amount of acetate produced was drastically reduced in strains containing the pyruvate decarboxylase enzyme from *Z. mobilis*, and ethanol appeared as the major fermentation product.

Under anaerobic conditions, lactate was the principal fermentation product that accumulated during 24 hr of growth of strain TC4 lacking a plasmid in rich medium containing glucose, with lesser amounts of acetate, succinate, and ethanol being present. Lactate production was dramatically reduced in strains containing the pyruvate decarboxylase enzyme and was accompanied by the production of substantial quantities of ethanol. It is likely that this lower level of accumulated ethanol was caused by the reduction in total cell mass produced under these anaerobic conditions, thus reducing the volumetric rate of ethanol production.

The extent of ethanol production under anaerobic and aerobic conditions was directly related to the level of expression of the *Z. mobilis* ethanologenic gene.

Derivatives of *E. coli* TC4 containing plasmids which express the ethanologenic enzymes from *Z. mobilis* grew to higher cell densities than did the parent organism lacking a plasmid. The increase in the final cell density, the extent to which ethanol accumulated in the medium, and the reduction in the rate of acidification of the culture broth during growth all correlated with the level of expression of pyruvate decarboxylase enzyme. Heterologous promoters were used to express the gene in order to minimize potential problems associated with transcriptional regulation.

It should be understood that the examples and embodiments described herein are for illustrative purposes only and that various modifications or changes in light thereof will be suggested to persons skilled in the art and are to be included within the spirit and purview of this application and the scope of the appended claims.

We claim:

1. A mutant *Escherichia coli* strain with a gene mutation, which results in hyperproduction of alcohol dehydrogenase which has been transformed with a *Zymomonas mobilis* gene coding for pyruvate decarboxylase, wherein said pyruvate decarboxylase gene is expressed at sufficient levels to confer upon said *Escherichia coli* transformant the ability to produce ethanol as a fermentation product.

2. The transformed *Escherichia coli*, according to claim 1, wherein said *Escherichia coli* is strain DC862 adhC or DC863 adhC adhR.

3. A method for the production of ethanol, said method comprising the growth of a mutant *Escherichia coli* with a gene mutation which results in hyperproduction of alcohol dehydrogenase which has been transformed with a *Zymomonas mobilis* gene coding for pyruvate decarboxylase, wherein said pyruvate decarboxylase gene is expressed at sufficient levels to confer upon said *Escherichia coli* transformant the ability to produce ethanol as a fermentation product.

4. The method, according to claim 3, wherein said *Escherichia coli* is strain DC862 adhC or DC863 adhC adhR.

* * * * *

UNITED STATES PATENT AND TRADEMARK OFFICE
CERTIFICATE OF CORRECTION

PATENT NO.    :   5,028,539

DATED         :   July 2, 1991

INVENTOR(S)   :   Lonnie O. Ingram and David P. Clark

It is certified that error appears in the above-identified patent and that said Letters Patent is hereby corrected as shown below:

Column 1    line 4:    Insert after title --This invention was made with government support under the following grants: USDA Alcohol Fuels Program #86CRCR12134 and DOE Office of Basic Energy FG0586ER3574. The government has certain rights in this invention.--

Signed and Sealed this

Twenty-third Day of March, 1993

Attest:

STEPHEN G. KUNIN

*Attesting Officer*    Acting Commissioner of Patents and Trademarks

UNITED STATES PATENT AND TRADEMARK OFFICE
CERTIFICATE OF CORRECTION

| | | |
|---|---|---|
| PATENT NO. | : 5,028,539 | Page 1 of 1 |
| APPLICATION NO. | : 07/274075 | |
| DATED | : July 2, 1991 | |
| INVENTOR(S) | : Lonnie O. Ingram | |

It is certified that error appears in the above-identified patent and that said Letters Patent is hereby corrected as shown below:

At Column 1, Line 6, after the period following the word "abandoned" please insert the following sentences:

--This invention was made, in part, with support by a grant from the United States Department of Energy (FG05-86ER3574). The Government has certain rights in the invention.--

Signed and Sealed this

Twenty-fifth Day of December, 2007

JON W. DUDAS
*Director of the United States Patent and Trademark Office*